United States Patent [19]

Lewicki

[11] Patent Number: 4,767,854

[45] Date of Patent: Aug. 30, 1988

[54] SEPARATION OF RDX AND HMX

[75] Inventor: Jerry W. Lewicki, Kingsport, Tenn.

[73] Assignee: The United States of America as represented by the Secretary of the Army, Washington, D.C.

[21] Appl. No.: 928,774

[22] Filed: Nov. 7, 1986

[51] Int. Cl.[4] .................. C07D 257/02; C07D 251/06
[52] U.S. Cl. .................................... 540/475; 544/215
[58] Field of Search ......................... 544/215; 540/475

[56] References Cited

U.S. PATENT DOCUMENTS

| 2,900,381 | 8/1959 | Thatcher | 544/215 |
| 3,133,054 | 5/1964 | Wright et al. | 544/215 |
| 3,676,425 | 7/1972 | Dawson et al. | 544/215 |

OTHER PUBLICATIONS

George et al., Ind. Eng. Chem., Prod Res. 2nd Dev. 4, 209 (1965).

Primary Examiner—Glennon H. Hollrah
Assistant Examiner—D. B. Springer
Attorney, Agent, or Firm—Robert P. Gibson; Edward Goldberg; Edward F. Costigan

[57] ABSTRACT

An RDX-HMX mixture containing a major amount of RDX is separated into essentially pure RDX and essentially pure HMX by first treating the mixture with DMSO to dissolve all the HMX present then recovering the remaining undissolved RDX as an essentially pure material. The dissolved mixture which contains a major amount of HMX and a minor amount of RDX is treated with cyclohexanone to dissolve all the RDX present, then the undissolved HMX remaining in the liquor is recovered as an essentially pure material.

4 Claims, No Drawings

SEPARATION OF RDX AND HMX

GOVERNMENT RIGHTS

The invention described herein may be manufactured, used and licensed by the Government for Governmental purposes without the payment to me of any royalties thereon.

BACKGROUND OF THE INVENTION

This invention relates to a method of separating RDX (cyclotrimethylene tetranitramine) and HMX (cyclotetramethylene tetranitramine) using a double cosolvent system.

RDX and HMX can be coproduced by a modified Bachmann reaction [Bachmann et al., J. Am. Chem. Soc., 71, 1842 (1979)] i.e. by the reaction of methenamine, ammonium nitrate and acetic anhydride. The resulting product can contain a 70/30 RDX/HMX by weight mixture. This process is more economical than Bachmann batch processes which produce very little HMX. In order to take advantage of the more economical production of RDX and HMX using the modified Bachmann process, it is necessary to develop a means to separate the RDX and HMX components as essentially pure products from the reaction mixture.

SUMMARY OF THE INVENTION

This invention is a method of separating, by using appropriate cosolvents, RDX as an essentially pure product from a mixture of RDX and HMX containing a major amount of RDX and a minor amount of HMX, e.g. a mixture produced by the nitrolysis of methenamine by the Bachmann process, which mixture contains about 70 parts by weight of RDX per 30 parts by weight of HMX. Essentially pure RDX can be obtained from any other mixture of RDX and HMX containing a major amount of RDX and a minor amount of HMX by the process of this invention. By "major amount" is meant from about 60 to 95 parts by weight of RDX per the "minor amount" of HMX, i.e. 40 to 5 parts by weight. The preferred amounts are 70/30 RDX/HMX.

In another aspect this invention is a method of separating, by using appropriate cosolvents, HMX as an essentially pure product from a mixture containing a major amount of HMX and a minor amount of RDX, e.g. a mixture obtained when essentially pure RDX is recovered from a mixture of a major amount of RDX and a minor amount of HMX, which mixture contains about 55 parts by weight HMX per 45 parts by weight RDX. Essentially pure HMX can be obtained from any other mixture of RDX and HMX containing a major amount of HMX and a minor amount of RDX. By "major amount" of HMX is meant 90 to 55 parts by weight HMX per "minor amount" of RDX, i.e. 10 to 45 parts by weight RDX.

The process of this invention is accomplished by treating the mixture of the major amount of RDX and the minor amount of HMX with water and DMSO (dimethyl sulfoxide) to preferentially extract substantially all the HMX therefrom, leaving the mother liquor essentially pure RDX. After filtering, the DMSO filtrate which contains a major amount of HMX, e.g. about 55 parts HMX per a minor amount of RDX, e.g. 45 parts RDX, is saturated with water to precipitate the solids which are then treated with cyclohexanone which preferentially dissolves the RDX component leaving essentially pure HMX in the filtrate liquor.

DETAILED DESCRIPTION

Although this invention can separate any mixture of RDX and HMX into its component parts, it has been found that the most efficient separation occurs when there is, on a weight basis, from 60 to 95 parts RDX to 40 to 5 parts HMX in the initial mixture, preferably 70 parts RDX to 30 parts HMX. In addition, although the invention is described in terms of treating a reaction mixture resulting from the Bachmann reaction, the source of the mixture of the RDX and HMX components is not critical to this invention.

The solvents used in this invention are those which are cosolvents for RDX and HMX but exhibit a preference for one of the components.

It has been found that DMSO exhibits a differential solubility characteristic which favors higher HMX solubility. For example, a DMSO solution saturated with both RDX and HMX at 30 degrees C. displays cosolubility constants of 25.1 grams/100 grams solvent for RDX and 44.0 grams/100 grams solvent for HMX. The HMX component, therefore, is approximately 1.75 times more soluble than the RDX component in saturated DMSO at 30 degrees C. Thus, according to this invention essentially pure RDX is isolated from a mixture with HMX by dissolving all the HMX from the mixture with DMSO. Only if there is a large enough amount of RDX in comparison to the amount of HMX, i.e. from 60 to 95 parts by weight RDX per 40 to 5 parts by weight HMX, is the process efficient, enabling essentially all the HMX to be removed and a large amount of the originally present RDX to remain in the mother liquor and be recovered as an essentially pure product. After treatment with DMSO and filtration, an RDX -HMX filtrate containing a major amount of the HMX component and a minor amount of the RDX component results. Generally, based on the amounts originally present, the filtrate contains about 10 to 45 parts RDX per 90 to 55 parts HMX.

In order to efficiently remove the RDX from this mixture, a solvent with a differential solubility which favors RDX is used. For example, a cyclohexanone solution saturated with RDX and HMX at 30 degrees C. displays cosolubility constants of 8.1 grams/100 grams solvent for RDX an 2.5 grams/100 grams solvent for HMX. The RDX component, therefore, is approximately 3.2 times more soluble than the HMX component in saturated cyclohexanone at 30 degrees C. Thus, extraction of an RDX-HMX mixture with a major amount of HMX and a minor amount of RDX in an amount of cyclohexanone sufficient to solubilize essentially all the RDX results in leaving essentially pure HMX in the residual filtrate liquor.

The temperature of determining the cosolubility constants does not have to be 30 degrees C., any temperature which does not affect the stability of the components can be used, however, 30 degrees C. is used generally for convenience.

Other solvents which may be used because their solubility characteristics favor HMX isolation are 1,2-dichloroethane, N,N,-dimethylformamide, propionic acid, n-butyl formate, nitrobenzene, acetone and ethyl propionate.

A solvent with solubility characteristics favoring the isolation of RDX is sulfolane.

In order to determine the grams of DMSO cosolvent to use to solubilize or extract all of the HMX component in an admixture of a major amount of RDX and a minor amount of HMX when no water is present, the following equation is used:

$$\text{Grams of cosolvent} = \frac{100 \times H}{S_H}$$

wherein H is the quantity of grams of HMX in the mixture and $S_H$ is the HMX cosolubility constant in grams/100 grams solvent.

If water is initially present in the mixture, the amount of cosolvent (preferably DMSO) required for extraction will be dependent on the variations in the HMX solubility properties and water content. The following equation is used to determine the amount of cosolvent to use:

$$\text{Grams of cosolvent} = \frac{100 \times H}{S_H^1} - W$$

wherein H is grams of HMX in the mixture $S_H^1$ is the HMX solubility (grams/100 grams solution) at a specific solvent(DMSO)-water concentration and W is the amount in grams of water present.

In the first step of the process, an RDX-HMX(70/30) mixture is combined with an optimum quantity of DMSO as calculated using the above equations, and agitated for approximately one hour at about 30 degrees C. to extract the HMX component. Following extraction, the slurry is filtered to isolate the undissolved RDX component. The remaining mother liquor is saturated with water to precipitate the filtrate having a major amount of HMX and a minor amount of RDX(generally 55 to 45 parts by weight respectively).

The HMX component is recovered from the precipitated filtrate which contains an approximately 40 parts RDX per 60 parts HMX by extracting the mixture with a sufficient amount of a cosolvent, preferably cyclohexanone, to dissolve the RDX component. The amount of cosolvent required for optimum recovery of the RDX component is calculated from the following equation:

$$\text{Grams of cosolvent} = \frac{100 \times R}{S_R}$$

wherein R is the grams of RDX present in the mixture and $S_R$ is the cosolubility constant in grams of RDX per 100 grams solvent in the solvent(cyclohexanone) at a specific extraction temperature.

Since cyclohexanone and water are immiscible, the presence of water does not alter the RDX and HMX cosolubility properties.

In the second step, an RDX-HMX(40/60) filtrate is combined with the cosolvent, preferably cyclohexanone, and agitated for about an hour at about 30 degrees C. The undissolved HMX component is then receovered by filtration.

The following Example illustrates the invention but is not intended to be limiting.

EXAMPLE (a) 100 grams of a mixture of 70 parts by weight RDX and 30 parts by weight HMX is combined with 66.7 grams of water and 322.8 grams of DMSO. The mixture is agitated at about 30 degrees C. for about one hour. The resulting slurry is filtered, washed with water and the recovered solids dried, weighed and analyzed to determine RDX purity. The solids weigh 46.6 grams and are 99+% pure RDX.

The resulting filtrate is then saturated with 500 milliliters of water and the precipitated solids are recovered by filtration. The precipitated solids are washed with water, dried, weight and analyzed for HMX content. The filtrate solids weigh 50.8 grams and are 45% RDX and 55% HMX.

(b) 66.7 grams of a 45/55 RDX/HMX mixture from part (a) herein containing 16.7 grams of water is added to 278 grams of cyclohexanone. The mixture is agitated at about 30 degrees C. for about one hour and then filtered at about 30 degrees C. to isolate the HMX component. The recovered solids are dried, weighed and analyzed to determine HMX purity. The solids weigh 18.6 grams and are 98+% pure HMX.

I claim:

1. A method of separating a mixture initially containing between about 60 and 95 parts by weight by RDX and between about 5 and 40 parts by weight of HMX to recover essentially pure RDX and essentially pure HMX which consists essentially of:
    (a) agitating said mixture with a sufficient amount of water and dimethyl sulfoxide at about 30° C. for about 1 hour, said dimethyl sulfoxide and water being a cosolvent for RDX and HMX having a cosolubility constant preference for HMX to dissolve essentially all the HMX present;
    (b) filtering the essentially pure undissolved RDX from the slurry resulting from step (a);
    (c) precipitating the filtrate from step (b) by saturating said filtrate with water to recover a solid having as a major component HMX and as a minor component RDX;
    (d) agitating the precipitate of step (c) with cyclohexanone at a temperature of about 30° C. for about 1 hour to dissolve essentially all of the RDX present, said cyclohexanone being a solvent for HMX and RDX having a cosolubility constant preference for RDX; and
    (e) filtering the essentially pure undissolved HMX from the mixture resulting from step (d) at a temperature of about 30° C.

2. The process of claim 1 wherein cyclohoxanone is replace with a solvent selected from the group consisting of
1,2-dichloroethane,
N,N-dimethylformamide,
propionic acid,
N-butylformate,
nitrobenzene,
acetone, and
ethyl propionate.

3. The process of claim 1 wherein the amount of water-dimethyl sulfoxide cosolvent in step (a) is determined by the formula:

$$\text{Grams of cosolvent} = \frac{100 \times H}{S} - W, \text{ wherein}$$

H is HMX in grams, S is HMX solubility in grams per 100 grams of solution at a specific cosolvent concentration, and W is water expressed as grams.

4. The process of claim 1 wherein the amount of cyclohexanone is step (d) is determined by the formula:

$$\text{Grams of cyclohexanone} = \frac{100 \times R}{SR}, \text{ wherein:}$$

R is RDX in grams present in the mixture, SR is RDX solubility in grams per 100 grams of cyclohexanone at a specific temperature.

* * * * *